United States Patent [19]

Newsome et al.

[11] Patent Number: 4,505,926
[45] Date of Patent: Mar. 19, 1985

[54] QUATERNARY AMINO IMIDAZOLIDINES, COMPOSITIONS AND USE

[75] Inventors: Peter M. Newsome, Cheam; Stephen F. Moss, Carshalton; Lee J. Beeley, Dorking; Malcolm N. Burgess, Horsham, all of England

[73] Assignee: Beecham Group p.l.c., England

[21] Appl. No.: 532,525

[22] Filed: Sep. 15, 1983

[51] Int. Cl.$^3$ .................. A61K 31/415; C07D 233/50
[52] U.S. Cl. .................................. 514/398; 548/315; 514/867
[58] Field of Search ..................... 548/315; 424/273 R

[56] References Cited

U.S. PATENT DOCUMENTS 4,450,170 5/1984 Beeley et al. ........................ 548/315
4,461,904 7/1984 York .................................... 548/315

OTHER PUBLICATIONS

European Patent Application 81,923, (6-22-83).

Primary Examiner—Robert W. Ramsuer
Attorney, Agent, or Firm—Hopgood, Calimafde, Kalil, Blaustein & Judlowe

[57] ABSTRACT

Compounds of formula (I):

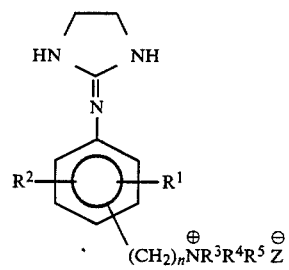

wherein
$R^1$ and $R^2$ are the same or different and each is selected from halogen, alkyl, haloalkyl, alkoxy and alkoxyalkyl,
$R^3$, $R^4$ and $R^5$ are the same or different and each is alkyl;
n is 0,1,2 or 3; and
Z is a pharmaceutically or veterinarily acceptable anion, protect animals from death due to enteropathogenic E. coli infection of the gastro-intestinal tract.

7 Claims, No Drawings

QUATERNARY AMINO IMIDAZOLIDINES, COMPOSITIONS AND USE

The present invention relates to quaternary aminophenyliminoimidazolidines and to their use in treating diarrhoea in humans and scours in animals, particularly to treatment of enterotoxin induced diarrhoea.

According to the present invention there is provided a compound of formula (I):

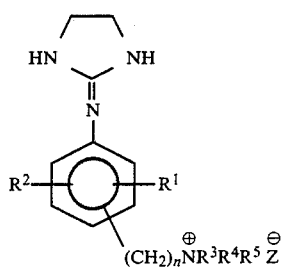

wherein $R^1$ and $R^2$ are the same or different and each is selected from halogen, alkyl, haloalkyl, alkoxy and alkoxyalkyl, $R^3$, $R^4$ and $R^5$ are the same or different and each is alkyl;

n is 0,1,2 or 3; and

Z is a pharmaceutically or veterinarily acceptable anion, and salts thereof.

Suitably, the alkyl and alkoxy groups mentioned above each have from 1 to 6 carbon atoms; those having 3 or more carbon atoms may be straight or branched chains.

Suitable haloalkyl groups include those having 1,2 or 3 halogen atoms, particular examples being trifluoromethyl and 2,2,2-trichloroethyl groups.

Preferably $R^1$ and $R^2$ are the same and each is methyl or chloro.

Preferably $R^1$ and $R^2$ are located in the 2,6 positions in relation to the imidazolidinimino group.

Suitable pharmaceutically or veterinarily acceptable anions include halide, hydroxide, sulphate and hydrogen sulphate anions, or carboxylate such as acetate or citrate.

Suitable salts include pharmaceutically or veterinarily acceptable salts, but it is not essential that salts are pharmaceutically or veterinarily acceptable as such salts may also be useful in producing or purifying the desired compound of formula (I). Pharmaceutically and veterinarily acceptable salts include acid addition salts with pharmaceutically or veterinarily acceptable salts, including hydrochloric, hydrobromic, hydroiodic, nitric, sulphuric, citric, lactic, maleic, pamoic and tartaric acids.

The compounds of formula (I) have advantages in the treatment of diarrhoea and scours, especially hypersecretory diarrhoeas and protect animals from death due to enteropathogenic *E. coli* infection of the gastrointestinal tract.

Accordingly, the present invention provides a compound of formula (I) for use in human or veterinary medicine, especially for use in treating or preventing diarrhoea in humans and scours in animals.

The present invention also provides a process for producing a compound of formula (I), which process comprises either (a) reacting a compound of formula (II)

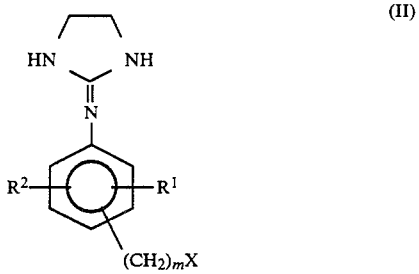

or a salt thereof, wherein $R^1$, and $R^2$ are as defined in relation to formula (I) and m is 1, 2 or 3 and X is a leaving group, preferably halogen with a compound of formula (III)

wherein $R^3$, $R^4$ and $R^5$ are as defined in relation to formula (I) or (b) reacting a compound of formula (IV)

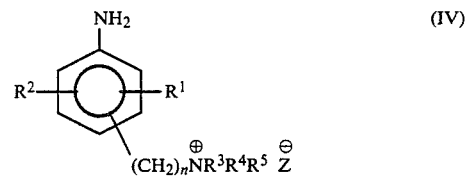

wherein $R^1$, $R^2$, $R^3$, $R^4$, $R^5$, n and $Z^\ominus$ are as defined in relation to formula (I)

with a compound of formula (V)

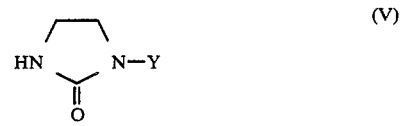

wherein Y is a protecting group and thereafter removing the protecting group, or (c) reacting a compound of formula (VI):

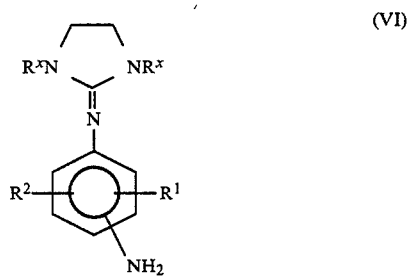

wherein $R^1$ and $R^2$ are as defined in relation to formula (I) and $R^x$ is a suitable protecting group with one or more alkyl halides and thereafter removing the protecting groups $R^x$.

The reaction of a compound of formula (II) with a compound of formula (III) is suitably conducted in an organic solvent, such as a lower alkanol, at ambient temperature. Advantageously a salt of the compound of formula (II), especially a hydrohalide salt is employed and the leaving group X forms the anion $Z^\ominus$ during the reaction.

The reaction of a compound of formula (IV) with a compound of formula (V) is suitably conducted in the presence of phosphoryl chloride at elevated temperature. The protecting group Y may be a conventional protecting group, such as an acyl group, for instance an acetyl group, and may be removed by conventional methods, such as by treating with an acid or base.

The reaction of a compound of formula (VI) with an alkyl halide may be effected under conventional conditions. Preferably an alkyl bromide is used. When $R^3$, $R^4$ and $R^5$ are different, appropriate alkyl halides may be used. The protecting groups $R^x$ are suitable conventional protecting groups, such as trialkylsilyl groups, especially trimethylsilyl groups, which may be removed under conventional conditions.

Compounds of formula (II), (IV) and (VI) are readily produced from known compounds, for instance using the reactions shown in Schemes I to IV:

SCHEME I

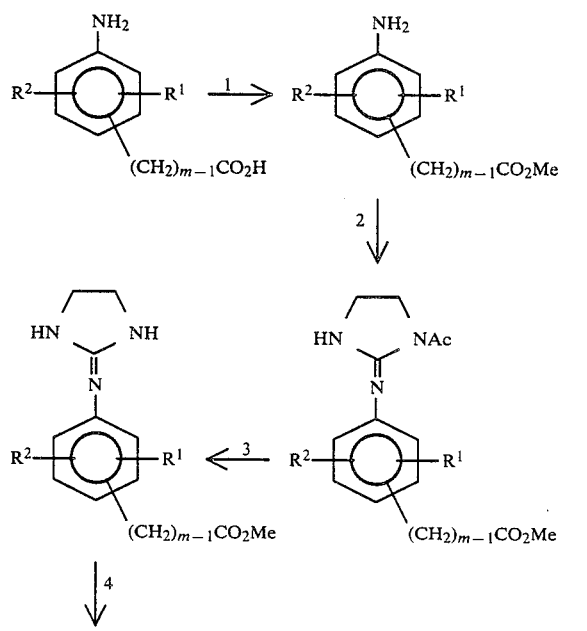

SCHEME I -continued

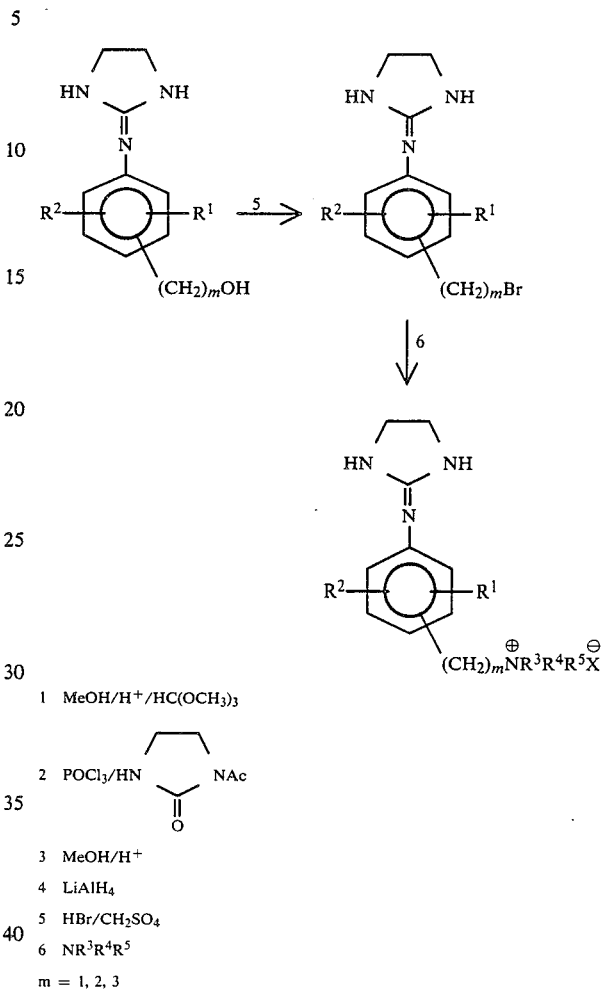

1  MeOH/H$^+$/HC(OCH$_3$)$_3$

2  POCl$_3$/HN⌒NAc with C=O

3  MeOH/H$^+$

4  LiAlH$_4$

5  HBr/CH$_2$SO$_4$

6  NR$^3$R$^4$R$^5$ m = 1, 2, 3

SCHEME II

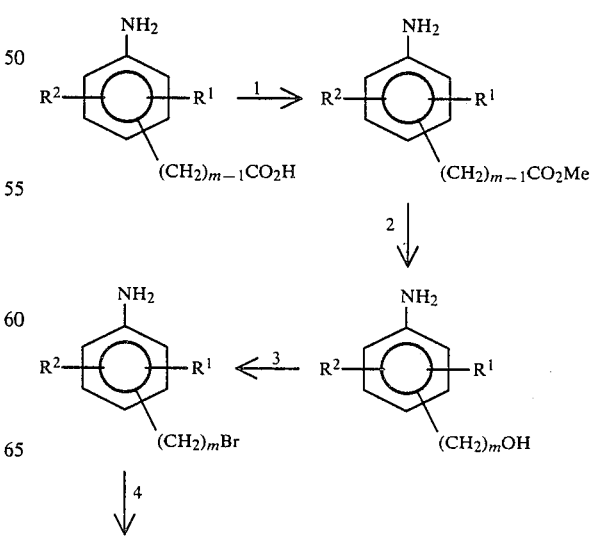

-continued
SCHEME II
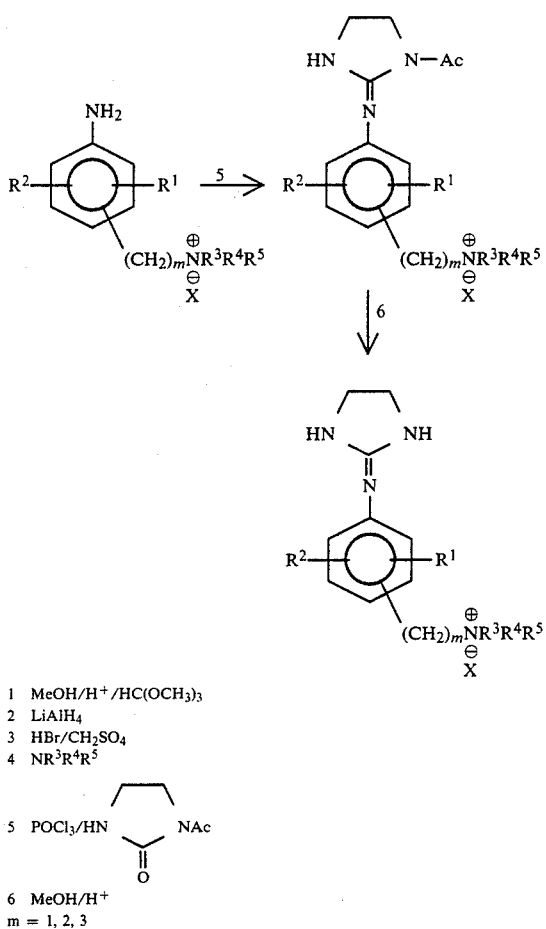
1 MeOH/H⁺/HC(OCH₃)₃
2 LiAlH₄
3 HBr/CH₂SO₄
4 NR³R⁴R⁵
5 POCl₃/HN⌐⌐⌐NAc (with C=O)
6 MeOH/H⁺
m = 1, 2, 3
SCHEME III
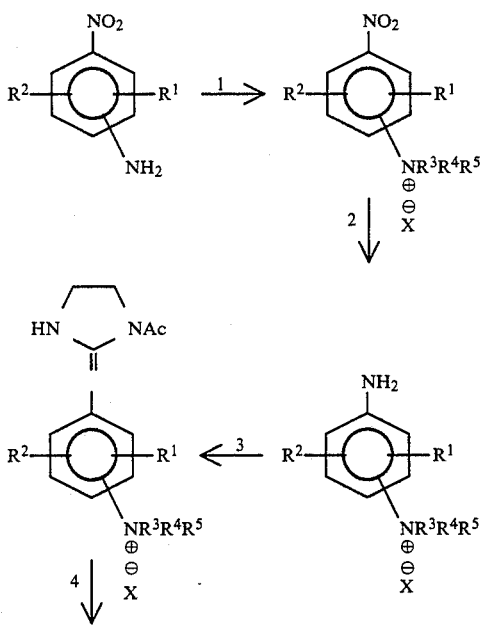
-continued
SCHEME III
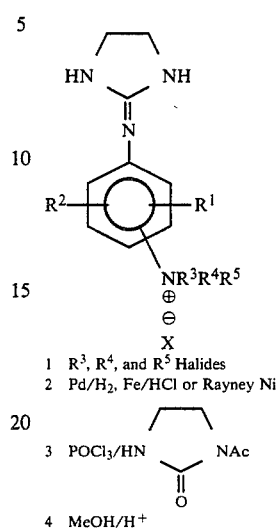
1 R³, R⁴, and R⁵ Halides
2 Pd/H₂, Fe/HCl or Rayney Ni
3 POCl₃/HN⌐⌐⌐NAc
4 MeOH/H⁺
SCHEME IV
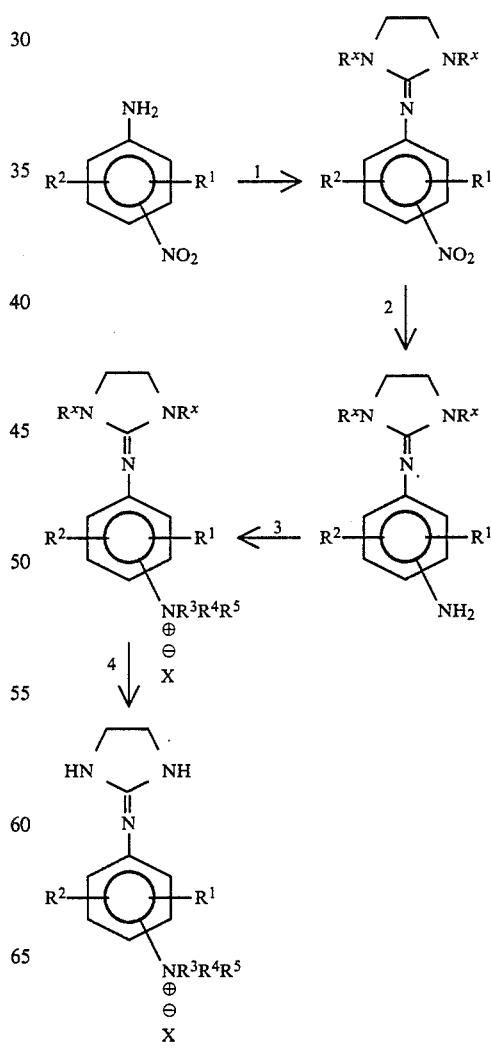

-continued
SCHEME IV

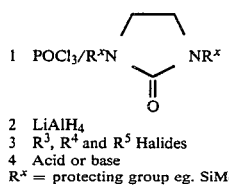

1. POCl$_3$/R$^x$N
2. LiAlH$_4$
3. R$^3$, R$^4$ and R$^5$ Halides
4. Acid or base R$^x$ = protecting group eg. SiMe$_3$ The present invention further provides a pharmaceutical or veterinary composition comprising a compound of formula (I) (hereinafter referred to as the "drug") and a pharmaceutically or veterinarily acceptable carrier therefor.

Pharmaceutical and veterinary compositions of the drug will, of course, be adapted for administration to the humans or animals to be treated. Thus, for example, the composition may be a shaped composition, such as a bolus, tablet or capsule. In such cases the pharmaceutically or veterinarily acceptable carrier will be chosen from the usual range of lubricants, dispersants, binders, fillers and the like. When these shaped compositions are for administration to cattle and pigs often they may for instance weigh at least 1 g, on occasions at least 2 g.

For administration to humans, especially children, the drug may suitably be presented as a syrup including suitable colouring and/or flavouring agents. Such syrups are conveniently presented in unit or multi-dose containers.

For veterinary use the composition may also be a dispersion or a solution of the drug in a suitable vehicle for use with an oral doser (this is a well known item of farm equipment, basically comprising a liquid reservoir, a mouthpiece adapted for insertion into animals mouths, and a pump mechanism whereby unit doses can be ejected from the reservoir through the mouthpiece). Conveniently the drug may be administered from an oral doser as an aqueous solution. Alternatively, the vehicle will be an oil or water based cream to ensure homogeneity of the unit doses administered.

The invention, therefore, also provides an oral doser containing a multi-dose of the drug in a veterinarily acceptable vehicle.

The drugs of the invention may also be added to the animal feed or drinking water. Thus the invention also provides animal feed or animal drinking water containing a compound of formula (I). It will be convenient to formulate these animal feed and drinking water compositions with a multi-dose of the drug so that the animal takes in an appropriate quantity of the drug along with its diet. It will also be convenient to present the composition of the invention as a pre-mix for addition to the feed or drinking water.

With human babies or young animals, a particularly useful technique is to blend their milk with the drugs of this invention.

The compositions of the invention may also be formulated for injection. In such cases the drug chosen is suitably dissolved in water for injection. Alternatively the drug may be administered in a solution used for parenteral fluid replacement therapy.

Often it will be appropriate to include in the compositions a further medicine such as an antibacterial agent for example an antibiotic such as amoxycillin or neomycin or a sulphonamide such as sulfadoxin, an agent to alter intestinal motility such as loperamide or a material such as pectin.

Treatment of diarrhoea and scours using the drug may be supplemented by oral rehydration therapy such as those described in U.K. Pat. No. 1,581,826 and German Offenlegungsschrift No. 28 54 281, U.K. patent application No. 2 012 163A, U.S. Pat. No. 3,898,328, Nalin, D. R. and Cash, R. A., Bull. World Health Org., 43, 361 (1970), French Pat. No. 2 467 599, U.K. Pat. No. 1 465 308 and as described in "Secretory Diarrhoea", Ed M. Field, J. S. Fordtran and S. G. Schultz, American Physiological Society, Maryland, 1980 pp 179–185 and Lancet, (1975) pp 79 and 80. Conveniently the drug may be administered with the oral rehydration formulation.

Accordingly the present invention provides, in a particular aspect, a formulation for treating diarrhoea which comprises an effective non-toxic amount of a compound of formula (I) as hereinbefore defined and an oral rehydration composition comprising a pharmacologically acceptable aqueous solution containing at least 0.5% w/v of an actively absorbed monosaccharide, at least 25 mM sodium ions and having an osmolarity less than 500 m Osmolar.

Preferably the oral rehydration composition further comprises actively-absorbed amino acids and electrolytes.

The drug may be presented as a formulation containing one or more components of the oral rehydration composition for admixture with the remaining components.

Alternatively the drug may be provided separately and administered simultaneously or sequentially with the oral rehydration formulation.

The amount of drug administered must, of course, be sufficient to bring about the desired effect and will also depend on the body weight of the recipient and the chosen route of administration. Typical dosages are in the range from 0.1 to 100 mg/kg particularly from 1 to 50 mg/kg. Useful dosage units based on such dosage would contain from 0.1 mg to 2500 mg of the drug, more suitably 1 mg to 2500 mg. Of course, it will be appreciated that many preferred compositions of the invention are in multi-dose form as, for the therapy of animals, it is often most desirable to be able rapidly to treat a number of animals. Such multi-dose compositions will contain, by way of example, at least 10 mg of the drug. Depending on the exact nature of the said multi-dose composition, often it will contain at least 250 mg of the drug, and on occasions as much as 25 g. Doses may be administered once or several times daily.

The present invention further provides a method for treating humans and animals, which method comprises administering an effective, non-toxic amount of a compound of formula (I) to the sufferer.

In a particular aspect the method of treatment comprises the administration of a pharmaceutical or veterinary composition of a compound of formula (I), as hereinbefore described.

The present invention will now be illustrated by the following Examples which are not intended to limit the invention in any way.

EXAMPLE 1

2,(2,6-Dichloro-4-triethylammoniomethyl-phenylimino)imidazolidine bromide

A solution of 2-(4-bromomethyl-2,6-dichlorophenylimino)imidazolidine hydrobromide (1.75 g, 4.3 mmol) in ethanol (60 cm$^3$) was added over 0.3 h to stirred triethylamine (8.75 cm$^3$) at room temperature. After 2.5 h the reaction mixture was evaporated to a colourless oil which was dissolved in chloroform (30 cm$^3$) and the solution cooled and left for 24 h. The suspended white solid was filtered, washed with chloroform and twice recrystallised from ethanol/diethyl ether affording prisms of 2-(2,6-dichloro-4-triethylammoniomethylphenylimino)imidazolidine bromide (1.04 g 2.5 mmol) m.p.>260° C.

Analysis calculated for $C_{16}H_{25}BrCl_2N_4$: Theory: C, 45.30; H, 5.93; Br, 18.81; Cl, 16.68; N, 13.19%. Found: C, 45.55; H, 5.85; Br, 18.74; Cl, 16.91; N, 13.11%.

$^1$H nmr (60 MHz) δH [(CD$_3$)$_2$SO]: 7.44 (s, 2H, Ar-H), 6.24 (br, 2H, NH), 4.43 (S, 2H, ArCH$_2$), 3.20 (q, 6H, CH$_2$CH$_3$), 1.30 ppm (t, 9H, CH$_2$CH$_3$)

EXAMPLE 2

2-(4-Bromomethyl-2,6-dichlorophenylimino)imidazolidine hydrobromide

Concentrated sulphuric acid (1.0 cm$^3$) was added dropwise to a stirred suspension of 2-(2,6-dichloro-4-hydroxymethylphenylimino)imidazolidine (2.34 g, 9.0 mmol) in 48% hydrobromic acid (4.7 cm$^3$). The suspension was heated to 100° C. for 1.5 h then cooled and diluted with acetone (20 cm$^3$). The suspended white prisms were filtered and identified as 2-(4-bromomethyl-2,6-dichlorophenylimino)imidazolidine hydrobromide (2.79 g, 6.9 mmol) m.p. 265°-6° C. (dec.).

Analysis calculated for $C_{10}H_{11}Br_2Cl_2N_3$: Theory: C, 29.73; H, 2.74; N, 10.38%. Found: C, 30.03; H, 2.64; N, 10.25%.

$^1$H nmr (60 Mz) δH [(CD$_3$)$_2$SO]: 10.60 (br, 1H, N$^{\oplus}$H), 8.59 (br, 2H, NH), 7.80 (S, 2H, Ar-H), 4.80 (s, 2H, CH$_2$Br), 3.80 ppm (s, 4H, (CH$_2$)$_{\overline{2}}$)

EXAMPLE 3

2-(2,6-dichloro-4-hydroxymethyl-phenylimino)imidazolidine

Lithium aluminium hydride (300 mg, 7.9 mM) was added to a stirred suspension of 2-(4-carbomethoxy-2,6-dichlorophenylimino)imidazolidine (750 mg, 2.6 mM) in dry tetrahydrofuran (50 ml) with stirring. The mixture was then stirred at room temperature for several hours after which time ethyl acetate was carefully added. The solvent was then removed under vacuum and water was added to the residue. After basification with dilute sodium hydroxide the aqueous mixture was extracted several times with ethyl acetate. The extract (750 mg) was dried and evaporated to give a solid which was recrystallised from isopropanol to give a white solid (330 mg) mp 208°-210° C.

Microanalysis: Calc. for $C_{10}H_{11}Cl_2N_3O$ C, 46.17; H, 4.26; N, 16.15%. Found: C, 46.23; H, 4.12; N, 15.9%.

EXAMPLE 4

2-(4-Carbomethoxy-2,6-dichlorophenylimino)imidazolidine

A solution of 1-acetyl-2-(4-carbomethoxy-2,6-dichlorophenylimino)imidazolidine (5 g, 15 mmole) and 2M hydrochloric acid (1 ml, 2 mmole) in methanol (100 ml) was heated under reflux for 40 hour. The mixture was then evaporated to give a solid which was taken up in methylene chloride/methanol (650 ml:30 ml) and extracted with saturated sodium carbonate (300 ml). The organic layer was dried and evaporated to give a residue which after trituration with ether, yielded the title compound as a solid (3.5 g) mp 229°-231° C.

Analysis calculated for $C_{11}H_{11}Cl_2N_3O_2$: Theory: C, 45.85; H, 3.85; N, 14.58. Found: C, 46.20; H, 3.83; N, 14.79.

EXAMPLE 5

1-Acetyl-2-(4-carbomethoxy-2,6-dichlorophenylimino)imidazolidine

Methyl-4-amino-3,5-dichlorobenzoate (16.8 g, 31 mmole), 1-acetyl-2-imidazolidone (4.3 g, 33.5 mmole) in phosphoryl chloride (44 ml) were stirred at 50° C. for 3 days. After cooling the phosphoryl chloride was evaporated to give an oily residue. Iced water was added to the residue which was then basified with aqueous sodium hydroxide. The mixture was extracted with methylene chloride which was then washed with water, dried (magnesium sulphate) and evaporated to give a creamy solid. This solid was recrystallised from toluene to give the title compound (7.7 g) mp 188°-189° C.

Analysis calculated for $C_{13}H_{13}Cl_2N_3O_3$: Theory: C, 47.30; H, 3.97; N, 12.73. Found: C, 47.34; H, 3.88; N, 12.60.

EXAMPLE 6

2-(2,6-Dichloro-4-trimethylammoniomethyl-phenylimino)imidazolidine bromide Hydrobromide.

A solution of 2-(4-bromomethyl-2,6-dichlorophenylimino)imidazolidine hydrobromide (2.5 g, 6.2 mmol) in ethanol (100 cm$^3$) was added over 0.8 h to stirred ethanolic trimethylamine (33%; 16 cm$^3$). The mixture was stirred at room temperature overnight, concentrated to an oil, which was then stirred with acetonitrile and the insoluble solid filtered. This solid was dissolved in hot methanolic hydrogen bromide and reprecipitated as colourless prisms (2.19 g, 92% yield) by addition of acetone. The product was identified as the title compound, m.p. 270°-5° C. (dec.).

Analysis calculated for $C_{13}H_{20}Br_2Cl_2N_4$: Theory: C, 33.72; H, 4.35; N, 12.10; Br$^-$, 34.51%. Found: C, 33.81; H, 4.38; N, 11.69; Br$^-$, 34.40%.

FORMULATION OF THE COMPOUNDS FOR VETERINARY ADMINISTRATION

Formulation 1

Compound of Example 1, Bolus

Boluses of the following composition were prepared:

| | |
|---|---|
| Compound of Example 1 | 100 mg |
| Microcrystalline cellulose | 500 mg |
| Corn starch | 250 mg |
| Magnesium stearate | 25 mg |
| Lactose, anhydrous | to 2500 mg |

The ingredients were passed through a 30 mesh stainless steel screen and blended in a suitable blender. The resultant compression mix was compressed directly on a tabletting machine to give tablets each containing 100 mg of the compound of Example 1.

Formulation 2

Oral Doser 5 mg/g

1 Kg of the following composition was prepared:

|  | % by wt. |
|---|---|
| Compound of Example 1 | 0.5 |
| Aluminium stearate | 6.0 |
| Sunflower oil | to 100 |

The aluminum stearate was dispersed with stirring in a portion of the sunflower oil heated to 115<C. The dispersion was added to the rest of the sunflower oil heated to 140<C. The gel was stirred at 130<C. for 15 minutes and then allowed to cool without stirring to room temperature. The milled compound of Example 1 was dispersed in the cooled gel base and then passed through a colloid mill to produce a fine, homogenous dispersion. The dispersion was filled into plastic bottles fitted with a dosing pump.

Formulation 3

Injection 5 mg/ml

1 Liter of the following composition was prepared:

|  | % w/v |
|---|---|
| Compound of Example 1 | 0.5 |
| Sodium chloride | 0.5 |
| Water for injections | to 100 |

The compound of Example 1 and sodium chloride were dissolved in the water for injections and the solution was filtered and sterilised by membrane filtration. The sterile solution was filled into glass ampoules.

Formulation 4

Soluble Powder

1 Kg of the following composition was prepared:

|  | % by wt. |
|---|---|
| Compound of Example 1 | 3.5 |
| Lactose | to 100 |

The compound of Example 1 and lactose were sieved and mixed together in a suitable blender to give a homogenous powder. The powder was filled into jars. The powder was used at the rate 0.5 g per gallon of drinking water to medicate pigs.

Formulation 5

Oral Rehydration Formulation containing the compound of Example 1

1 kg of the following composition was prepared by mixing together the ingredients in dry powder form:

| | |
|---|---|
| Glycine | 10.3% |
| Dextrose (anhydrous) | 67.6 |
| Sodium Chloride | 14.3 |
| Potassium Dihydrogen Phosphate | 6.8 |
| Citric Acid | 0.8 |
| Tri-potassium Citrate | 0.2 |
| Compound of Example 1 | 0.15 |

60 g of the composition was then dissolved in 2 liters of water and fed to diarrhoeic calves.

Formulation 6

The following formulation may be prepared by the method set out below:

| | |
|---|---|
| Compound of Example 1 | 0.5% w/v |
| Bentone 38[1] | 1.5% w/v (ie 1.5 g/100 ml) |
| Propylene Carbonate | 0.6% w/v |
| Pharmasorb[2] | 10% w/v |
| Phosphoric Acid[3] | 0.1% w/v |
| Ampicillin Trihydrate | 6.0% w/v as free acid |
| Soya-Bean Oil | to 100% |

[1] Bentone 38 is an amidé derivative of bentonite
[2] Pharmasorb is a brand of activated Attapulgite.
[3] The phosphoric acid is present to balance the alkaline pH of the Bentone.

The Bentone was dispersed in the soya-bean oil, and when thoroughly distributed, the propylene carbonate was added with high speed mixing, followed by colloid milling to produce the base. Into this base was first mixed the phosphoric acid, and then the pharmasorb, the penicillin, and the compound of Example 1 and the resultant suspension was then passed through a colloid mill once more.

Formulation 7

| | |
|---|---|
| Compound of example 1 | 6% w/w |
| Citric acid | 75% w/w |
| Sodium citrate* | 19% w/w |

*Sodium citrate may be replaced by sodium acetate or propionate.

The above formulation is added to oral rehydration solutions at the rate of 0.2-0.8 g/l and is fed to diarrhoeic calves.

BIOLOGICAL DATA

Protection of Neonatal Mice from Lethal Enteropathogenic E coli Infection 4 day old mice were orally dosed with 50 μl of phosphate buffered saline containing $1 \times 10^5$ organisms/ml of E. coli B44 (09:K90:K99) an enteropathogenic strain originally isolated from a scouring calf. The mice were then dosed b.i.d. with either placebo or drug for four days commencing 16 hours after infection. The animals were left with their mothers throughout the experiment and a daily record of deaths was made. The experiment was terminated when no mortality was seen over a 24 hour period. (Usually 7-10 days after infection). The mortality in the drug group was then compared with the mortality in the placebo group using the following formula:

$$\% \text{ Reduction in mortality} = \left[ \frac{Mp - Md}{Mp} \right] \times 100$$

where
Mp = mortality in group receiving placebo
Md = mortality in group receiving drug
Statistical analysis was performed using $2 \times 2$ contingency tables (single tailed 'p'). Results are given in Table 1.

TABLE 1

| Treatment | No of mice infected | No of mice dead after 10 days | % Mortality | % Protection by drug |
|---|---|---|---|---|
| Control | 70 | 38 | 54 | — |
| Example I (50 mg/kg) | 68 | 20 | 29 | 46* |
| Example I (10 mg/kg) | 68 | 22 | 32 | 40* |
| Control | 89 | 75 | 84 | — |
| Example 6 (10 mg/kg) | 73 | 52 | 71 | 15 |

*p 0.01 compared to control mortality.

We claim:

1. A compound of formula (I):

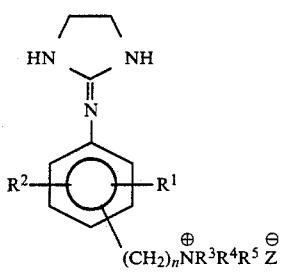

wherein

R$^1$ and R$^2$ are the same or different and each is selected from halogen, alkyl, haloalkyl, alkoxy and alkoxyalkyl, R$^3$, R$^4$ and R$^5$ are the same or different and each is alkyl;

n is 0,1,2 or 3; and

Z is a pharmaceutically or veterinarily acceptable anion, and salts thereof.

2. A compound as claimed in claim 1 wherein R$^1$ and R$^2$ are the same and each is methyl or chloro.

3. A compound as claimed in claim 1 wherein R$^1$ and R$^2$ are located in the 2,6 positions in relation to the imidazolidinimino group.

4. A compound as claimed in claim 1 and selected from 2,(2,6-Dichloro-4-triethylammoniomethylphenylimino)imidazolidine bromide and 2-(2,6-Dichloro-4-trimethylammoniomethylphenylimino)-imidazolidine bromide and salts thereof.

5. A pharmaceutical or veterinary composition comprising a compound of formula (I) as defined in claim 1 and a pharmaceutically or veterinarily acceptable carrier therefor.

6. A formulation for treating diarrhoea which comprises an effective non-toxic amount of a compound of formula (I) as defined in claim 1 and an oral rehydration composition comprising a pharmacologically acceptable aqueous solution containing at least 0.5% w/v of an actively absorbed monosaccharide, at least 25 mM sodium ions and having an osmolarity less than 500 m Osmolar.

7. A method for treating or preventing diarrhoea and scours in a human or non-human animal comprising administering an antidiarrhoeally effective, non-toxic amount of a compound as defined in claim 1 to the human or non-human animal.

* * * * *